United States Patent [19]

Okamoto et al.

[11] Patent Number: 4,600,784
[45] Date of Patent: Jul. 15, 1986

[54] HIGH PRESSURE SYNTHESIS OF SUBSTITUTED TETRATHIAFULVALENES

[75] Inventors: Yoshiyuki Okamoto, Ft. Lee; Joseph E. Rice, Waldwick, both of N.J.

[73] Assignee: Koppers Company, Inc., Pittsburgh, Pa.

[21] Appl. No.: 814,104

[22] Filed: Dec. 27, 1985

Related U.S. Application Data

[60] Continuation of Ser. No. 415,331, Sep. 7, 1982, abandoned, which is a division of Ser. No. 286,142, Jul. 9, 1982, abandoned.

[51] Int. Cl.$^4$ .............................................. C07D 339/06
[52] U.S. Cl. ....................................................... 549/39
[58] Field of Search .......................................... 549/39

[56] References Cited

U.S. PATENT DOCUMENTS 3,876,662  4/1975  Hartzler ........................ 542/453 X
4,312,992  1/1982  Green ............................... 549/39 X

FOREIGN PATENT DOCUMENTS 36414  3/1980  Japan.

OTHER PUBLICATIONS

Narita et al, Int. J. of Methods in Synthetic Organic Chemistry, No. 8 (1976) pp. 489–513.

*Primary Examiner*—Richard L. Raymond
*Attorney, Agent, or Firm*—Donald M. MacKay; Herbert J. Zeh, Jr.

[57] ABSTRACT

A process is disclosed for one-step preparation of substituted tetrathiafulvalenes by reaction of carbon disulfide with acetylenic compounds under pressures of at least about 1,000 atmospheres. Substituted tetrathiafulvalenes made by this process are particularly useful as precursors to very pure tetrathiafulvalene, a compound which can complex with tetracyano-p-quinodimethane to form a charge-transfer salt having very high electrical conductivity.

10 Claims, No Drawings

HIGH PRESSURE SYNTHESIS OF SUBSTITUTED TETRATHIAFULVALENES

This is a continuation of application Ser. No. 415,331, filed Sept. 7, 1982, now abandoned which is a division of application Ser. No. 286,142, filed July 23, 1981, now abandoned.

BACKGROUND OF THE INVENTION

1. Field of the Invention

Preparations of substituted tetrathiafulvalenes from reactions of carbon disulfide with various acetylenic compounds are well know. Of particular interest herein is a one-step method for synthesis of substituted tetrathiafulvalenes from reactions of carbon disulfide with an acetylenic compound under high pressure conditions.

2. State of the Art

Recent findings of the unusual electronic properties of complexes of tetrathiafulvalene (TTF) have generated increased interest in new synthetic routes for preparation of TTF and substituted TTF analogue-compounds. It has been found, for example, that TTF can complex with tetracyano-p-quinodimethane (TCNQ) to form a crystalline charge-transfer salt. This TTF.TCNQ salt, in which TTF is characterized as the electron-donor cation, exhibits metallic properties over a wide temperature range and has reportedly one of the highest electrical conductivities $(\sigma_{max} = 1.47 \times 10^4$ ohm$^{-1}$cm$^{-1}$ at 66° K.) of known organic materials [see Ferraris et al, *J. Am. Chem. Soc.*, 95, 948 (1973)].

The superior electrical properties of the TTF.TCNQ salt, a so-called "organic metal", make the salt a particularly likely candidate for many solid-state or physical-electronics applications. In such applications, materials of very high purity are usually required. Known preparations of TTF involve multi-step synthetic routes which typically produce TTF in low yields or in relatively impure form.

One synthetic route to TTF involves deprotonation of 1,3-dithiolium salts accomplished, for example, by coupling of 1,3-dithiolium hydrogen sulfate with a tertiary amine. Suitable thiolium salts for deprotonation to TTF are synthesized by the seven-step method of Klingsberg [Klingsberg, *J. AM. Chem. Sec.*, 86, 5290 (1964)], which method involves a complicated preparation of 1,3-dithiolium hydrogen sulfate starting from thiophosgene and disodium salt of dimercaptomaleonitrile. Another synthetic route, as devised by Wudl et al [*Chem. Commun.* 1453 (1970)], involves reaction of acetylene, sulfur and carbon disulfide to form 1,3-dithiole-2-thione, which thione compound is oxidized to 1,3-dithiolium hydrogen sulfate; a coupling reaction of this salt with triethylamine in acetonitrile yields TTF.

Increased yields and purity of small amounts of TTF have been reported by the step-wise reduction of commercially available 2-thiomethyl-1,3-dithiolium iodide with sodium borohydride to give 2-thiomethyl-1,3-dithiole as an oil, which oil when treated with fluoroboric acid forms 1,3-dithiolium fluoroborate; this compound on deprotonation with excess amine provides in high purity TTF [Wudl et al, *J. Org. Chem.*, 39, 3608 (1974)].

More suitable to large-scale preparation of TTF is a somewhat simplified version of the Klingsberg Method reported by Melby et al, *J. Org. Chem.*, 39, 2456 (1974). Melby's six-step method requires preparation of a diester, namely, dimethyl 1,3-dithiole-2-thione-4,5-dicarboxylate, which diester is hydrolyzed, under a two-hour reflux condition in the presence of hydrochloric acid and acetic acid, to its corresponding dicarboxylic acid; the diacid is subjected to a pyridine reflux to form a thione which is then converted to 1,3-dithiolium hydrogen sulfate, and thereafter a thiolium coupling salt is made with hexafluorophosphate; TTF is then formed by coupling reaction in the presence of a tertiary amine. Melby also reported synthesis of TTF in small amounts by reacting methyl propiolate, tributylphosphine and carbon disulfide in tetrahydrofuran at −30° C. The resulting diester, namely, 4,4'(5')-bis(carbomethoxy)-$\Delta^{2,2'}$-bi-1,3-dithiole, is subjected to alkaline hydrolysis to form the counterpart diacid, which diacid when decarboxylated provides TTF in an overall yield of about 13 percent based on methyl propiolate starting material.

In U.S. Pat. No. 3,876,662 to Hartzler, substituted TTF compounds are synthesized by reactions of carbon disulfide with various acetylenic compounds bearing electron-withdrawing groups. The starting materials typically are heated at about 100° C. for a period of two to four days, with the reaction carried out in a sealed container under autogeneous pressure. Hartzler discloses obtaining increased yield of substituted TTF compounds with the use of a catalyst provided by an organic acid having pKa less than about five.

SUMMARY OF THE INVENTION

Substituted tetrathiafulvalene compounds are prepared by subjecting a mixture of reactants to a pressure of at least about 1,000 atmospheres, those reactants comprising carbon disulfide and at least one compound containing an acetylenic moiety. The acetylenic compound may be expressed by the general formula ZC≡CZ wherein each of the Z substituents may be the same or different and is a member selected from the set consisting of the following groups:

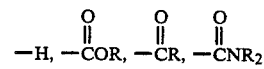

wherein R is selected from hydrogen and alkyl, aryl and alkaryl groups of up to about 12 carbon atoms. Where R is hydrogen in the illustrated structural groups, the Z substituent may be carboxyl group, aldehyde group and amido group, respectively. It is understood that in the amido group structure, each of the two R groups may be hydrogen, alkyl or aryl substituents, or any combination thereof, so as to embrace primary, secondary and tertiary amido groups. The starting compound containing the acetylenic moiety is further characterized by at least one of the Z groups being an electron-withdrawing substituent.

A principal advantage of the present invention is that substituted tetrathiafulvalenes are provided by a one-step reaction, as compared to known synthetic routes requiring six or more steps. Moreover, the process of the invention may be carried out in the absence of catalyst. Inasmuch as contaminating catalysts are not required in the present process, substituted TTF compounds of exceptional purity can be prepared, which compounds are useful as precursors to obtaining tetrathiafulvalene (TTF). Moreover, synthesis of troublesome by-products is less likely in the single-step process of the invention as compared to multi-step preparations.

High purity TTF is particularly useful as an electron-donor cation in charge-transfer salts such as provided by complexes of TTF and tetracyano-p-quinodimethane (TCNQ).

DETAILED DESCRIPTION OF THE INVENTION

The terms "high pressure synthesis" or "high pressure reactions" as used herein are intended to describe preparation of fulvalene compounds by subjecting certain reactants to a pressure of at least about 1,000 atmospheres for a time and at a temperature sufficient fo form fulvalene compounds. The term "fulvalene compound" is intended to embrace products made by the process of the invention, which products contain the basic structural configuration of tetrathiafulvalene (TTF) [also known as 1,3-dithiole-2-(1,3-dithiol-2-ylidene)] depicted in formula I:

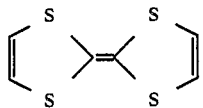
(I)

Such fulvalene compounds may be prepared by processes utilizing the step depicted generally in equation II:

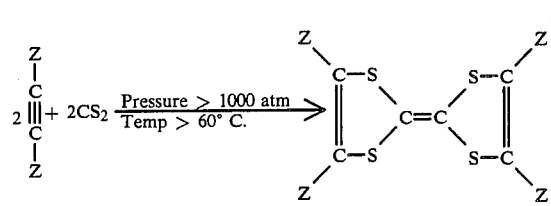
(II)

wherein the Z groups are substituents as defined before. Expected substitute tetrathiafulvalene reaction products will be found as both cis- and transisomers. The process is particularly suitable for preparing substituted tetrathiafulvalenes useful as precursors to obtaining relatively pure quantities of tetrathiafulvalene (TTF).

Preferred acetylenic starting materials for making substituted TTF compounds include compounds of the general type $ZC\equiv CZ$ wherein at least one of the Z groups is an electron-withdrawing substituent selected from carboxyl group, carboxyl aliphatic ester groups and amido groups.

Carboxyl and carboxyl aliphatic ester groups suitable as Z substituents may be further defined as members of a class embraced by empirical formula III:

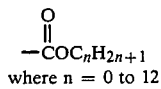
(III)

where n = 0 to 12 with such Z substituents being attachable to the TTF structure at the carbonyl carbon of the Z substituent. Carboxyl group as a Z substituent is typified by carboxyl group contained in formic acid. Carboxyl aliphatic ester groups as the Z substituent are typified by groups contained in the esterification products of formic acid with an aliphatic alcohol of one to about 12 carbon atoms. Representative straight-chain aliphatic alcohols include methyl, ethyl, n-propyl, n-butyl, n-pentyl, n-hexyl, n-heptyl, n-octyl, n-nonyl, n-decyl and n-dodecyl alcohols. Representative branched-chain aliphatic alcohols include isopropyl, isobutyl, sec-butyl, tert-butyl, isopentyl, amyl and tert-pentyl alcohols.

Examples of amido group substituted acetylenic compounds include acetylene carboxamide, acetylene dicarboxamide, propiolic carboxamide, propiolic dimethylcarboxamide, acetylene bis(dimethylcarboxamide), propiolic diethylcarboxamide, propiolic dipropylcarboxamide, acetylene bis(diethylcarboxamide), acetylene bis(dipropylcarboxamide), propiolic dioctylcarboxamide and acetylene bis(dinonylcarboxamide).

Particularly preferred acetylenic starting materials for reacting with carbon disulfide in preparation of substituted TTF compounds are acetylenic-containing compounds such as methyl propiolate, propiolic acid, dimethyl acetylenedicarboxylate and acetylene dicarboxamide. Substituted TTF compounds prepared from these starting materials will have structures as shown in Equation II with Z substituents selected from the group consisting of hydrogen,

In the reaction of carbon disulfide with methyl propiolate, or with dimethyl acetylenedicarboxylate, or with a mixture of both esters, as the acetylenic starting material, an intermediate structure is formed as shown in formula IV:

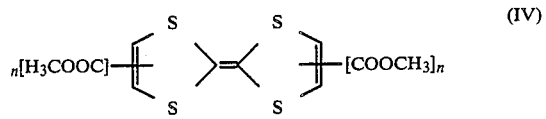
(IV)

wherein "n" may be 1 or 2. Formula IV embraces di, tri, or tetra-ester substituted TTF compounds including cis- or trans- isomers of such compounds. Such intermediate compounds may be subjected step-wise to firstly alkaline hydrolysis to form a carboxylic acid salt, which carboxylic acid salt may then be subjected to acid hydrolysis to form a carboxylic acid derivative, which derivative may then be decarboxylated to yield tetrathiafulvalene. Alkaline hydrolysis may be accomplished by subjecting the intermediate of Formula IV to refluxing conditions in the presence of aqueous or alcoholic sodium or potassium hydroxide. Acid hydrolysis of the resulting salt may be accomplished by acidification with a strong inorganic acid, such as hydrochloric and sulfuric acids. Decarboxylation of the carboxylic acid derivative may be accomplished by heating the derivative to 240° C. in the presence of pyridine in a sealed vessel.

In the reaction of carbon disulfide with propiolic acid as the acetylenic starting material, an intermediate is formed having the structure V:

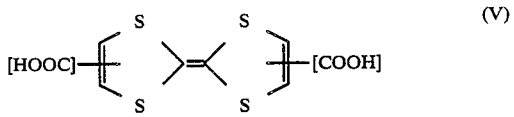
(V)

Formula V embraces di-substituted TTF compounds including the cis- or transisomers. These intermediates may be decarboxylated to tetrathiafulvalene under decarboxylation conditions like those outlined above for the Formula IV intermediates.

In the reaction of carbon disulfide with acetylene carboxamide, or with acetylene dicarboxyamide, or with a mixture of both amides, as the acetylenic starting material, an intermediate structure is formed as shown in Forumla VI:

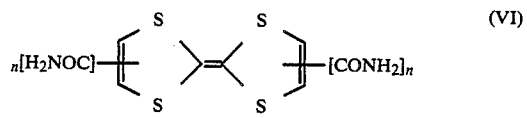

wherein "n" may be 1 or 2. Formula VI embraces di, tri, or tetra-amide substituted TTF compounds including cis- or trans- isomers of such compounds. Such intermediate amide-substituted compounds may be subjected sequentially to alkaline hydrolysis, acid hydrolysis and decarboxylation steps, as described above for the Formula IV intermediates, to yield TTF.

It has been found that effective synthesis of TTF and substituted TTF compounds is achieved by a combination of suitable temperature and pressure conditions. For example, when acetylenic compounds and $CS_2$ are subjected to pressures as high as 4500 atmospheres, synthesis does not go forward at temperatures around 20° C. Generally, reaction temperatures of at least about 60° C. are required, and temperatures in a range from about 70° C. to about 110° C. are preferred; reaction temperatures in a range from 70° C. to about 90° C. are especially preferred. Reaction temperatures greater than about 120° C. should be avoided inasmuch as unwanted by-products may form at such higher temperatures. While pressures of at least about 1000 atmospheres are generally effective in the described process, reaction pressures of about 2000 atmospheres or greater are preferred.

In order to demonstrate the process of the invention, reactions of carbon disulfide with four acetylenic compounds were carried out under varying reaction conditions of temperature, time and pressure. In all cases except one, good yields of very pure substituted TTF compounds were obtained under high pressure conditions at reaction temperatures of 80° C. or higher. In the synthesis of TTF dicarboxylic acid, yield was lower in one high pressure run at a relatively higher temperature, as compared to yields obtained in other high pressure preparations of TTF dicarboxylic acid and TTF ester. This one low-yield run may be attributed to decomposition of the TTF dicarboxylic acid product to TTF and $CO_2$ inasmuch as $CO_2$ was evolved during the reaction.

The high pressure reactions were run in Teflon capsule having a three-ml capacity. The capsule was mounted in a steel die equipped with a heating band; pressure was applied with a Clifton 200-ton hydraulic press. Acetylenic compound starting materials were obtained from Aldrich Chemical Co., Milwaukee, Wis., and were used as received without further purification. Infrared spectra for reaction products dispersed in KBr pellets were recorded on a Perkin-Elmer Model 457 grating IR Spectrophotometer; melting point determinations were made using an electro-thermal melting point apparatus.

EXAMPLE I

A starting mixture was prepared by dissolving 5 ml of methyl propiolate (56 mmol) in 15 ml of carbon disulfide (250 mmol). A three-ml capacity Teflon reaction capsule was filled with a portion of this starting mixture, there being substantially no free-space above the reaction mixture. Pressure was applied to the contents of the reaction vessel and maintained at 5,000 atm., ±200 atm., for a period of about 26 hours, while the temperature was maintained at about 100° C. The capsule was allowed to cool to room temperature over a period of about two hours. The capsule was opened and found to contain a dark red solid material in contact with a small amount of red liquid. The solid material was isolated from the liquid, washed several times with small quantities of $CS_2$, and then dried under reduced pressure. A dark brown solid material in an amount of 1.28 g was obtained equivalent to a 96 percent yield, based upon the amount of methyl propiolate used. The dark brown material had a melting point of 236°–240° C. After recrystallization of the dark brown material from 1,2-dimethoxy ethane solvent, red crystals were obtained having a melting point of 242°–244° C. The red crystal product, characterized by IR peaks at 3060, 3040, 1700, 1580, 1250 and 820 $cm^{-1}$, was identified as 4,4'(5')-bis(carbomethoxy)tetrathiafulvalene.

EXAMPLE II

The high pressure reaction of methyl propiolate and $CS_2$ was repeated under conditions substantially as set out in Example I, except that the pressure applied was 4,000 atm., the temperature of reaction was 80° C. and the reaction time was about 24 hours. A dark brown solid material was obtained in an amount of 1.18 g, equivalent to a yield of 88 percent. Qualitative determinations of the reaction product confirmed the presence of relatively pure compound identified as 4,4'(5')-bis(carbomethoxy)tetrathiafulvalene.

EXAMPLE III

A starting mixture was prepared by dissolving 5 ml of dimethyl acetylenedicarboxylate (41 mmol) in 15 ml of carbon disulfide (251 mmol). Conditions of reaction were repeated substantially as set out in Example I, above, with a pressure of 5,000 atm., ±200 atm., applied to the contents of the reaction vessel, heated to a temperature of about 100° C. for about 24 hours. A dark red solid material was obtained in an amount of 0.8 g, equivalent to an 87 percent yield based upon the amount of dimethyl acetylenedicarboxylate used. This product, isolated and washed as described before, was found to have a melting point of 162°–167° C. Recrystallization of this product from ether-hexane solution yielded red crystals having a melting point of 163°– 167° C. The product, characterized by IR peaks at 1740, 1720, 1575 and 1225 $cm^{-1}$, was identified as 4,4',5,5'-tetrakis(carbomethoxy)tetrathiafulvalene.

EXAMPLE IV

A starting mixture was prepared by dissolving 5 ml of propiolic acid (81 mmol) in 10 ml of methylene chloride. To this mixture was added 15 ml of carbon disulfide (251 mmol). Conditions of reaction were repeated substantially as set out in Example I, above, with a pressure of 5500 atm., ±200 atm., applied to the contents of the reaction vessel, heated to a temperature of about 85° C. for about 19 hours. Upon opening of the reaction vessel after cooling to room temperature, $CO_2$ gas was found to have evolved from the reaction mixture. A black solid material was removed from the capsule, and then treated sequentially by the steps of washing with $CS_2$, dissolving 1N NaOH, filtering, acidifying with 2N HCl, and then drying the product overnight under reduced pressure at 60° C. A crystalline product was obtained in an amount of 0.82 g, equivalent to a yield of 69 percent based upon propiolic acid starting material. The product, found to have a melting point of 360° C. (literature ref: 360° C.) and characterized by IR peaks at 3500, 2500, 1660 and 1550 cm$^{-1}$, was identified as tetrathiafulvalene-4,4'(or 5')-dicarboxylic acid.

EXAMPLE V

The high pressure reaction of propiolic acid and CS$_2$ was repeated under conditions substantially as set out in Example IV, except that the temperature was maintained at 95° C. over a 26 hour period. Discharge of a relatively large amount of CO$_2$ gas was noted upon opening of the reaction vessel indicating substantial decomposition of TTF acid product to TTF and CO$_2$. A black solid material was obtained in an amount of 0.24 g, equivalent to a yield of 20 percent. This relatively low yield was likely due to the in situ spontaneous decomposition of the product as indicated by the discharge of CO$_2$ gas. Qualitative determinations of the solid material, treated as described in Example IV, confirmed the presence of relatively pure compound identified as tetrathiafulvalene-4,4'(or 5')-dicarboxylic acid.

EXAMPLE VI

A starting mixture was prepared by dissolving 441 mg of acetylene dicarboxamide (3.9 mmol) in 30 ml of dimethyl formamide with mild heating. To this mixture was added 5 ml of carbon disulfide (84 mmol). A three-ml capacity Teflon reaction capsule was filled with a portion of this starting mixture, there being substantially no free-space above the reaction mixture. Pressure was applied to the contents of the reaction vessel and maintained at 6,000 atm., ±200 atm., for a period of about 24 hours, while the temperature was maintained at about 95° C. The capsule was allowed to cool to room temperature over a period of about two hours. The capsule was opened and found to contain a reddish-brown solid material in contact with a small amount of liquid. The solid material was isolated from the liquid, washed several times with small quantities of ethyl ether, and then dried under reduced pressure. A dark brown solid material was obtained in good yield. The dark brown material had a melting point above 360° C. After recrystallization of the dark brown material from acetone solvent, brown crystals were obtained having a melting point above 360° C. The brown crystal product, characterized by IR peaks at 3340, 3180, 3070, 3050, 1660,1590, 1260, 1125, 1090, 1030, 845, 795, 730, 700, and 480 cm$^{-1}$, was identified as 4,4',5,5'-tetrakis(carboxamide)-tetrathiafulvalene.

Although specific examples of the instant invention have been set forth hereinabove, it is not intended that the invention be limited solely thereto, but is to include all the variations and modifications falling within the scope of the appended claims.

What is claimed is:

1. A process for preparing a fulvalene compound, said process comprising the step of subjecting a mixture of reactants in the absence of a catalyst to a pressure of at least about 1,000 atmospheres, for a time and at a temperature between about 70° C. and 110° C. to form said fulvalene compound, said reactants comprising carbon disulfide and at least one compound containing an acetylenic moiety of the general formula

ZC≡CZ wherein each of the Z substituents may be the same or different and is a member selected from the set consisting of the following groups -H and

wherein R is selected from OCH$_3$, OC$_2$H$_5$, OH and NH$_2$; with the proviso that at least one of the Z substituents is an electron withdrawing group.

2. The process of claim 1 wherein the fulvalene compound is a substituted tetrathiafulvalene and said compound containing an acetylenic moiety is methyl propiolate, propiolic acid, dimethyl acetylene-dicarboxylate, or acetylene dicarboxamide.

3. The process of claim 1 wherein the step of subjecting a mixture of reactants comprises carbon disulfide and methyl propiolate to a pressure of at least about 4,000 atmospheres to provide an intermediate having the structure

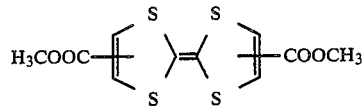

4. The process of claim 1 wherein carbon disulfide and methyl propiolate are subjected to a pressure of at least about 4,000 atmospheres to provide an intermediate having the structure

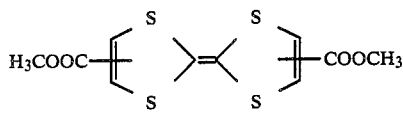

and said intermediate is subjected to alkaline hydrolysis to form a salt, which salt may be subjected to acid hydrolysis to form a carboxylic acid derivative, which carboxylic acid derivative may be subjected to decarboxylation to form tetrathiafulvalene.

5. The process of claim 1 wherein a mixture of reactants comprising carbon disulfide and propiolic acid is subjected to a pressure of at least about 4,000 atmospheres to provide an intermediate having the structure

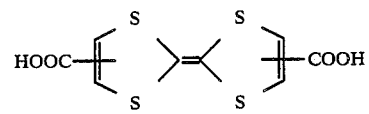

6. The process of claim 1 wherein carbon disulfide and propiolic acid are subjected to a pressure of at least about 4,000 atmospheres to provide an intermediate having the structure

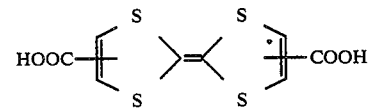

and subjecting said intermediate to decarboxylation to form tetrathiafulvalene.

7. The process of claim 1 wherein a mixture of reactants comprising carbon disulfide and dimethyl acetylene-dicarboxylate are subjected to a pressure of at least about 4,000 atmospheres to provide an intermediate having the structure

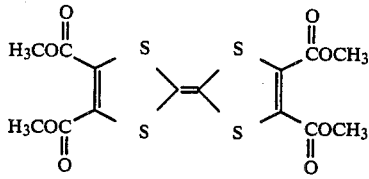

8. The process of claim 1 wherein an intermediate is formed from carbon disulfide and dimethyl acetylene dicarboxylate of the structure

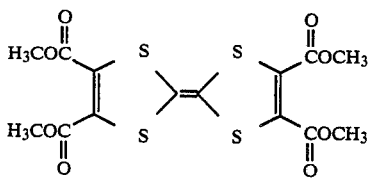

and said intermediate is subjected to alkaline hydrolysis to form a salt, which salt may be subjected to acid hydrolysis to form a carboxylic acid derivative, which carboxylic acid derivative may be subjected to decarboxylation to form tetrathiafulvalene.

9. The process of claim 1 wherein a mixture of reactants comprising carbon disulfide and acetylene dicarboxamide are subjected to a pressure of at least about 4,000 atmospheres to provide an intermediate having the structure

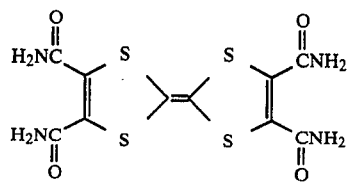

10. The process of claim 1 wherein an intermediate is formed from a mixture of reactants comprising carbon disulfide and acetylene dicarboxamide subjected to a pressure of at least about 4,000 atmospheres to provide an intermediate having the structure

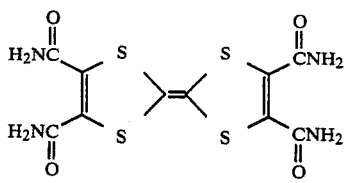

and said intermediate is subjected to alkaline hydrolysis to form a salt, which salt may be subjected to acid hydrolysis to form a carboxylic acid derivative, which carboxylic acid derivative may be subjected to decarboxylation to form tetrathiafulvalene.

* * * * *